United States Patent [19]

Frisch

[11] Patent Number: 4,615,704
[45] Date of Patent: Oct. 7, 1986

[54] SHAPE RETENTION TISSUE EXPANDER AND METHOD OF USING

[75] Inventor: Eldon E. Frisch, Midland, Mich.

[73] Assignee: Dow Corning Corporation, Midland, Mich.

[21] Appl. No.: 674,457

[22] Filed: Nov. 26, 1984

[51] Int. Cl.[4] .............................................. A61F 2/12
[52] U.S. Cl. ....................................... 623/8; 128/1 R
[58] Field of Search ............... 128/1 R, DIG. 25, 346; 3/1, 36

[56] References Cited

U.S. PATENT DOCUMENTS

| | | | |
|---|---|---|---|
| 3,665,520 | 5/1972 | Perras et al. | 3/36 |
| 3,934,274 | 1/1976 | Hartley | 3/36 |
| 4,157,085 | 6/1979 | Austad | 128/1 R |
| 4,205,401 | 6/1980 | Frisch | 3/36 |
| 4,217,889 | 8/1980 | Radovan et al. | 128/1 R |

FOREIGN PATENT DOCUMENTS 2199266 3/1974 France .

OTHER PUBLICATIONS

Data Sheet–"Silastic ® Percutaneous Skin Expander", No. L080-0011, Jan. 1983, Dow Corning Wright, Arlington, Tenn. 38002, 4 pages.
Data Sheet, "Radovan TM Subcutaneous Tissue Expander", Heyer Schulte Corporation, No. 101513-001-0-4-1079, V. Mueller, distributor, Chicago, Ill. 60648, 4 pages, undated.
Preliminary Data Sheet–"CUI Skin Expander–Saline-Fill Skin Expander", Cox-Uphoff International, Santa Barbara, Calif. 93103, 4 pages, undated.
Data Sheet–"Saline Fill Skin & Tissue Expander", No. 120060-8206, Cox-Uphoff Intl., Santa Barbara, Calif. 93103, 2 pages.
Advertisement–"CUI Skin and Tissue Expanders", No. 83-66-0928, Cox-Uphoff Intl., Santa Barbara, Calif. 93103, 1 page.

Primary Examiner—Richard J. Apley
Assistant Examiner—David J. Isabella
Attorney, Agent, or Firm—Richard E. Rakoczy

[57] ABSTRACT

This invention relates to an implantable, inflatable dual chamber shape retention tissue expander having a resilient annular base and a generally hemispherical shape after inflation which is used to form a generally hemispherical pocket beneath the tissue to be expanded to, for example, provide an appropriately shaped pocket for the receipt of an implantable mammary prosthesis and to a method of using such a tissue expander.

4 Claims, 5 Drawing Figures

SHAPE RETENTION TISSUE EXPANDER AND METHOD OF USING

BACKGROUND OF THE INVENTION

This invention relates to an implantable, inflatable dual chamber shape retention tissue expander having a resilient annular base and a generally hemispherical shape after inflation which is used to form a generally hemispherical pocket beneath the tissue to be expanded to, for example, provide an appropriately shaped pocket for the receipt of an implantable mammary prosthesis and to a method for using such a tissue expander.

Various types of human tissue expanders are commercially available: SILASTIC ® Percutaneous Skin Expander from Dow Corning Wright, Arlington, Tenn. 38002; the RADOVAN TM Subcutaneous Tissue Expander from Heyer-Schulte Corporation, Goleta, Calif. 93017 which is described in U.S. Pat. No. 4,217,889 to Radovan, et al. (issued Aug. 19, 1980) and the CUI Skin Expander from Cox-Uphoff International, Santa Barbara, Calif. 93103. These tissue expanders are implanted and filled percutaneously (usually with an isotonic saline solution) gradually over an extended time period for use in post mastectomy reconstruction techniques to prepare a pocket for receipt of an implantable mammary prosthesis, for use in the correction of hypoplasia or to generate additional tissue for use in scar revision procedures. Austad, in U.S. Pat. No. 4,157,085 (issued June 5, 1979), teaches an osmotically expandable tissue expander which does not require percutaneous inflation.

A problem inherent in prior art tissue expanders is that the tissue overlying the implanted tissue expander resists stretching as the tissue expander is inflated which causes the tissue expander to be forced into the shape of a sphere as it is inflated. The Radovan, et al, Patent teaches that the tissue expander must have a base which is inflexible or stiffly flexible to prevent possible damage to underlying tissue from pressure exerted by the tissue expander as it is inflated and also to control the shape of the skin enlargement obtained upon inflation. If the base is flexible, the base can curl on inflation. A pocket having the desired shape is more difficult to obtain when such curling occurs.

Rapid inflation can result in tissue necrosis, so gradual inflation over an extended period of time is the preferred practice. A capsule of fibrous contractile tissue can form around the tissue expander over the period of time during which the tissue expander is being gradually inflated, again tending to force the tissue expander into a spherical shape which results in a spherical pocket. A hemispherical pocket is preferred for post mastectomy reconstruction since the tissue expander is removed and replaced, for example, by a silicone gel-filled, silicone elastomer mammary prosthesis which has a generally hemispherical shape to replace the breast removed during the mastectomy procedure.

One example of an implantable mammary prosthesis is the SILASTIC ® II Mammary Implant H.P. sold by Dow Corning Wright. Another example is the implant described in my U.S. Pat. No. 4,205,401 (issued June 3, 1980) entitled "Mammary Prosthesis Which Resists Capsular Contracture". The prosthesis described in my '401 patent is a sac which is filled with a filler material such as a silicone gel and further contains a restraining means for resisting the tendency for surrounding tissue to form the prosthesis into the undesirable shape of a sphere after implantation. This device is intended for long-term implantation into an existing pocket beneath the skin although the prosthesis can be filled with gel or other filler material after it is inserted into a pocket beneath the skin to reduce the size of the incision needed to implant the prosthesis. This prosthesis is not filled to its capacity, but is only filled with a sufficient amount of filler material to give the prosthesis a low profile shape and to give it a pliant responsive nature over its broad surfaces. The restraining means within the sac can be an annular ring filled with a filler material such as silicone gel to render it reactive to tissue pressure and to resist the tendency of surrounding tissue to form the prosthesis into a sphere.

SUMMARY OF THE INVENTION

It is one object of this invention to provide a shape retention tissue expander for temporary implantation beneath tissue to be expanded to provide a generally hemispherical pocket for the later implantation of a mammary prosthesis.

Another object of this invention is to provide a tissue expander which resiliently resists forces applied to it during the time it is being inflated to maintain its shape and expand the overlying tissue in the desired manner.

These and other objects of the present invention are provided by a shape retention tissue expander which consists essentially of two separately inflatable envelopes wherein one envelope surrounds the lower portion of and forms a base for the other envelope which has a generally hemispherical shape such that upon inflation of the envelope forming the base, that inflated envelope forms a resilient annular base which acts to resiliently resist forces exerted by surrounding tissue during the inflation to deform the other envelope during the period of inflation from a generally hemispherical shape to a spherical shape.

This invention also relates to a method of expanding tissue to form a generally hemispherical pocket using such a device.

BRIEF DESCRIPTION OF THE DRAWINGS

The above and other objects and advantages of the present invention will become apparent to those skilled in the art upon an examination of the following description and drawings which are illustrative of the present invention.

In the Drawings.

DETAILED DESCRIPTION OF THE INVENTION

Figure 1:
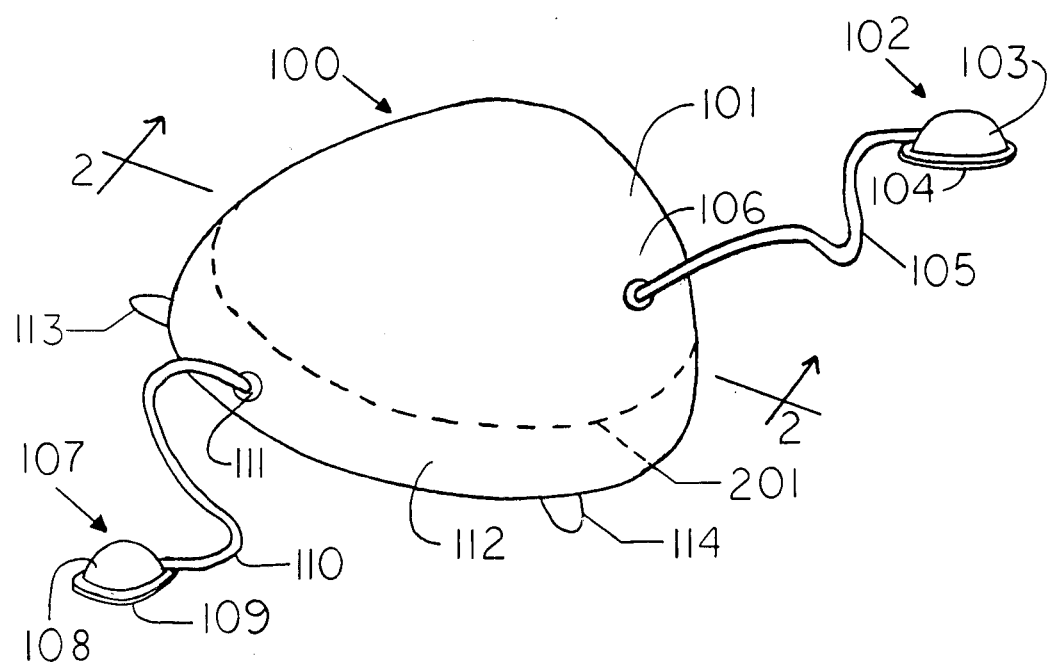
FIG. 1 is a perspective view of a shape retention tissue expander of the present invention shown inflated.
Figure 2:
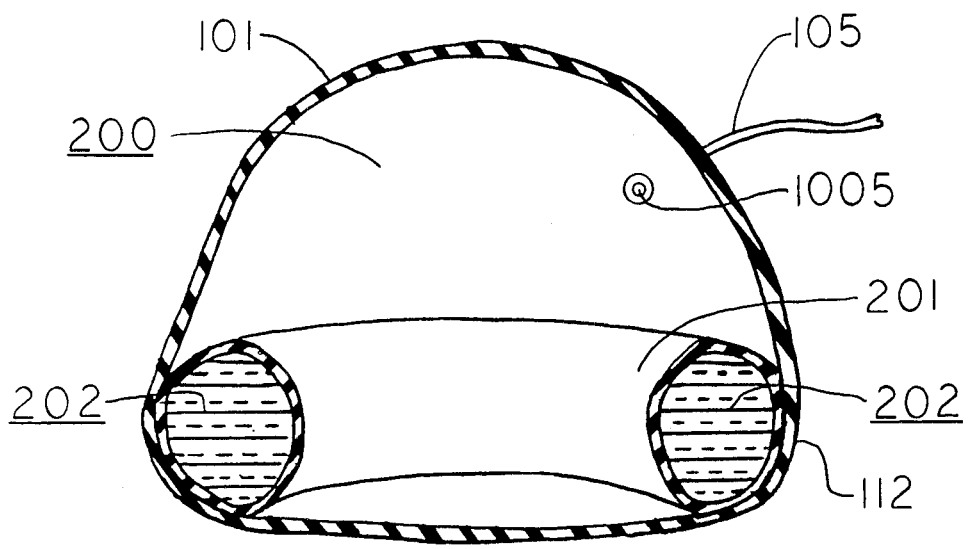
FIG. 2 is a cross-section taken along line 2—2 of FIG. 1 with the fluid used to inflate the outer envelope being omitted for clarity.

Referring to the Drawings, FIGS. 1 and 2 depict a preferred form of a shape retention tissue expander 100 which is composed of an outer envelope 101 having a generally hemispherical shape after complete inflation having a means for inflating and thus pressurizing the envelope. That inflation means is shown in the form of injection button 102 of conventional design having a self-sealing hollow dome 103 of, for example, biocompatible silicone elastomer mounted to a flat base 104 to permit inflation by addition of fluid such as isotonic saline solution into the interior region 200 of envelope 101.

A hypodermic needle is used to introduce fluid into the hollow region beneath dome 103. It travels through the center 1005 of tube 105 which can be of a biocompatible silicone elastomer up to attachment point 106 by which tube 105 is sealed such as by means of a silicone adhesive to the surface of envelope 101 such that the center 1005 of tube 106 is in communication with the interior region 200 of envelope 101. Similarly, the second envelope 201, which after inflation forms an annular resilient base surrounding the lower portion 112 of envelope 101, also contains a separate injection button 107 having a hollow dome 108 attached to a flat base 109 such that fluid injected through dome 108 travels through the center of tube 110 up to attachment point 111 by which tube 110 passes through envelopes 101 and 201 and is in sealing communication with the interior region 202 of envelope 201. One example of an injection button that can be used is found in U.S. Pat. No. 4,190,040 to Schulte (issued Feb. 26, 1980). In alternative embodiments, one or both of the above remote inflation means could be mounted directly on the envelope and an injection button of the type described in U.S. Pat. No. 4,428,364 to Bartolo (issued Jan. 31, 1984) could be used.

Interior region 202 of envelope 201 is shown as containing a fluid which is preferably an isotonic saline solution although other biocompatible fluids which will remain under pressure within each envelope, such as a silicone gel, could also be used. Region 200 would also contain a fluid when inflated as shown in FIGS. 1 and 2, but the fluid has been omitted from the figures for the purposes of clarity.

Envelopes 101 and 201 are preferably constructed of a biocompatible silicone elastomer such as one of the medical grade silicone elastomers commonly used in the manufacture of mammary implants or tissue expanders (e.g., those which are available from Dow Corning Corporation, Midland, Mich. 48640), but could be manufactured of any other biocompatible elastomer material such as a polyurethane material.

Envelope 201 is employed to provide an annular resilient base for the lower portion 112 of the expander 100, but need not have a circular cross-section as shown in FIG. 2. Likewise, envelope 201 may be formed separate and apart from envelope 101 as shown in FIG. 2 or may be integral with the lower portion 112 of envelope 101. Envelope 201 may also be affixed to the exterior rather than the interior of the lower portion 112 of envelope 101.

To insure that the lower portion of expander 100 remains opposite the tissue to be expanded so that the tapering upper portion of the hemispherical pocket is ultimately formed away from the body in the tissue being expanded, lower portion 112 can contain an external means such as fixation tabs 113 and 114 (further containing corresponding opposing tabs—not shown) attached to the bottom of portion 112 for suturing or ingrowth to underlying tissue. Similarly, the attachment means could take the form of a conventional polyester tissue ingrowth material or a backing situated across the bottom of lower portion 112 of expander 100 in place of fixation tabs.

Figure 3:
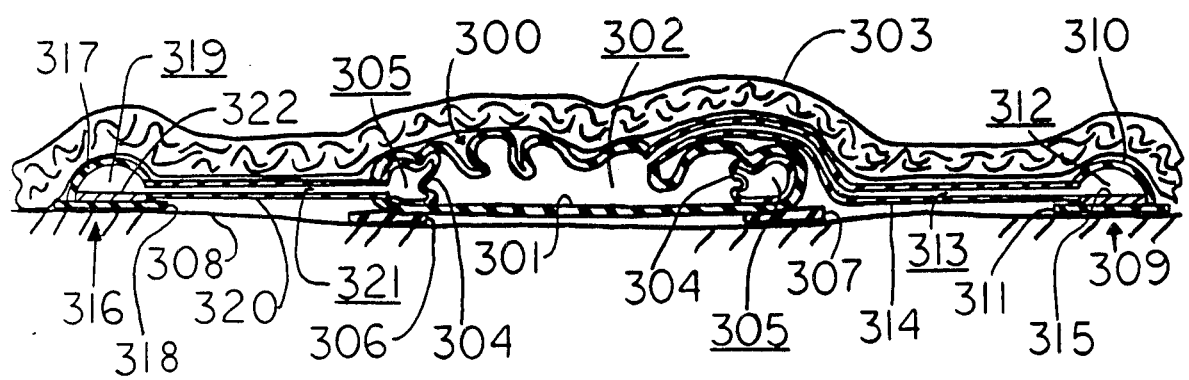
FIG. 3 is a sectional side view of an uninflated tissue expander implanted beneath the skin.
Figure 4:
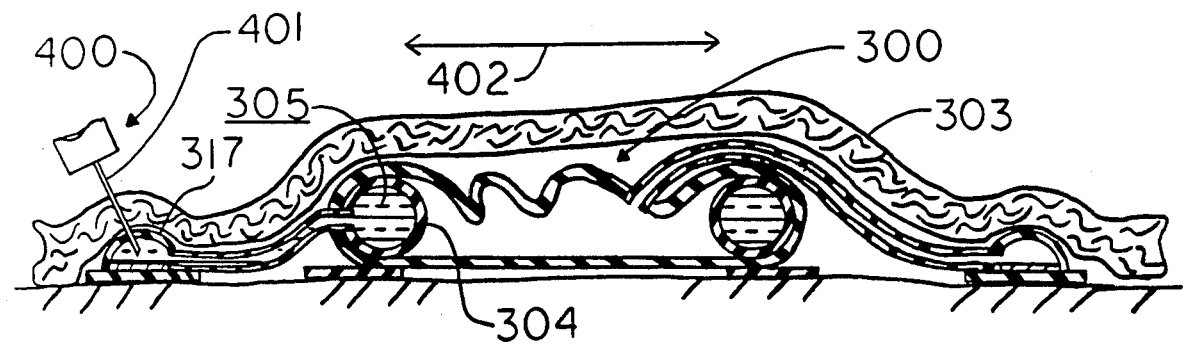
FIG. 4 is a sectional side view showing the inner annular envelope forming the base fully inflated.
Figure 5:
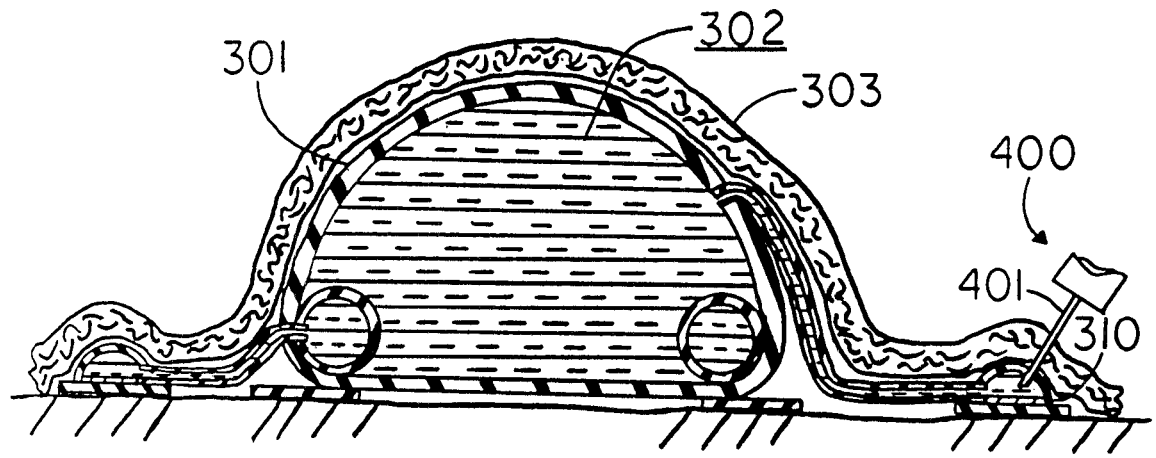
FIG. 5 is a sectional side view showing the entire tissue expander fully inflated to form a generally hemispherical pocket beneath the skin.

Having described the tissue expander, the manner in which it can be used will now be described with reference to FIGS. 3-5. In FIG. 3, a sectional side view of deflated shape retention tissue expander 300 (of the same type as that shown in FIGS. 1 and 2) having outer envelope 301 of biocompatible silicone elastomer and hollow interior region 302 has been implanted beneath the tissue 303 to be expanded (e.g., at the site where a female breast had been previously removed) according to operative techniques familiar to those skilled in the art of implantation of tissue expanders. The lower portion of expander 300 containing inner envelope 304 of biocompatible silicone elastomer with hollow interior region 305 surrounds the lower portion of envelope 301 to form an annular base after inflation of envelope 304 is completed. Fixation tabs 306 and 307 are sutured to underlying tissue 308 (e.g., fascia on the chest wall where expander 300 is being used in post mastectomy reconstructive surgery).

Expander 300 contains an inflation button 309 having a self-sealing dome 310 and a flat base 311 which forms a hollow interior region 312 which is in sealing communication with interior region 302 of envelope 301 by means of the hollow center 313 of tube 314. A metal needle stop 315 is fixed to base 311 to prevent a hypodermic needle from passing completely through button 309. Similarly, envelope 304 is inflated by means of injection button 316 having a self-sealing dome 317 and a flat base 318 which forms a hollow interior region 319 which is in sealing communication with interior region 305 of envelope 304 by means of the hollow center 321 of tube 320. A metal needle stop 322 is fixed to base 319 to prevent a hypodermic needle from passing completely through button 316. Inflation buttons 309 and 316 are also implanted beneath tissue 303 at some distance from the expander 300. Tubes 314 and 320 may each contain check valves or disconnecting fittings along the tube of the type described in the Radovan, et al. patent to enable one or both injection buttons to be removed if desired at some point after inflation of the expander 300 has begun.

In practicing the method of this invention, syringe 400 is filled with isotonic saline and hypodermic needle 401 is passed through skin 303 and through dome 317 to accomplish the gradual inflation of envelope 304 with the saline solution over a period of several days to several weeks. During inflation, tissue 303 is stretched laterally in the direction of arrows 402 until the envelope 304 is pressurized to an adequate extent to form a resilient base which will resist forces by the surrounding tissue and any fibrous contractile tissue which may form around expander 300. The same level of pressurization upon inflation as was described in my '401 Patent described above can be employed in this application to inflate the envelope forming the resilient base: at least about 5 grams per square centimeter. Upon complete inflation, as shown in FIG. 4, skin 303 has stretched laterally in the direction of arrows 402 and has also raised away from underlying tissue 308 to form a disk-shaped, generally flat pocket.

Upon complete inflation of envelope 304, envelope 301 is inflated gradually over a period of several weeks in accordance with accepted tissue expansion techniques to avoid necrosis of the skin being expanded. As shown in FIG. 5, syringe 400 is filled with isotonic saline solution to enter region 302 of envelope 301 until envelope 301 is fully inflated and develops a generally hemispherical pocket. Upon full inflation, expander 300 is surgically removed and a conventional mammary prosthesis of a preselected size suited to match the size of the pocket developed is implanted in the pocket remaining upon removal of expander 303 to complete the method of the present invention.

While the invention has been described with reference to post mastectomy reconstruction procedures, other modifications and variations of the expander and method of the present invention will become apparent to those skilled in the art upon an examination of the above Specification and Drawings. Therefore, other variations of the present invention may be made which fall within the scope of the appended claims even though such variations were not specifically discussed above.

That which is claimed is:

1. A method of expanding tissue to form a generally hemispherical pocket which comprises the steps of
   (I) implanting beneath the tissue to be expanded a shape retention tissue expander consisting essentially of (A) a first inflatable biocompatible envelope having a generally hemispherical shape containing a first means for inflating said first envelope with a biocompatible fluid material and (B) a second inflatable biocompatible envelope which surrounds the lower portion of and forms a base for said first envelope, said second envelope containing a second means for inflating said second envelope with a biocompatible fluid material wherein said second envelope forms an annular resilient base about the lower portion of said first envelope after inflation to resiliently resist forces exerted by surrounding tissue to deform the first envelope during inflation from a generally hemispherical shape to a spherical shape,
   (II) inflating said second envelope gradually over a period of time to expand the tissue laterally and form a generally flat pocket and thereafter
   (III) pressurizing said first envelope gradually over a period of time to expand the tissue upward way from the base formed by said second envelope to complete formation of a generally hemispherical pocket,
   (IV) removing said expander, and
   (V) implanting a mammary prosthesis in place of the expander.

2. The method as claimed in claim 1 wherein Step I comprises implanting a shape retention tissue expander of the type described in Step I wherein said envelopes are made of a biocompatible silicone elastomer.

3. The method as claimed in claim 1 wherein said expander has an external means for fixing the expander to tissue underlying the tissue to be expanded to maintain the desired orientation of the expander beneath the tissue to be expanded and prior to Step II, the fixation tabs are positioned opposite the tissue to be expanded in contact with tissue formerly underlying the tissue to be expanded.

4. The method as claimed in claim 1 wherein Step I comprises implanting a shape retention tissue of the type described in Step I wherein said second envelope is contained within said first envelope.

* * * * *